United States Patent [19]

Drake

[11] 4,446,308

[45] May 1, 1984

[54] POLYMER RESIDUE TREATMENT

[75] Inventor: Charles A, Drake, Bartlesville, Okla.

[73] Assignee: Phillips Petroleum Company, Bartlesville, Okla.

[21] Appl. No.: 393,282

[22] Filed: Jun. 29, 1982

[51] Int. Cl.³ .............................................. C08F 8/50
[52] U.S. Cl. .................................... 528/481; 549/461
[58] Field of Search ........................ 528/481; 549/461

[56] References Cited

U.S. PATENT DOCUMENTS 2,683,151  7/1954  Hillyer et al. .................... 260/346.2
2,816,878  12/1957  Harvey et al. .................... 260/45.5
3,016,701  1/1962  Kolfenbach et al. ............. 60/39.08
3,232,849  2/1966  Renberg ............................. 203/51
3,232,850  2/1966  Renberg et al. ..................... 203/58

OTHER PUBLICATIONS

*Ind. and Eng. Chem.* 40, 2216 (1948).

Primary Examiner—Stanford M. Levin

[57]  ABSTRACT

A process for producing additional useful products from the cotrimer reaction product formed by the reaction of a diolefin and a furfural which comprises pyrolyzing the polymeric residue of the reaction product to form additional quantities of diolefin, furfural and cotrimer product.

8 Claims, No Drawings

POLYMER RESIDUE TREATMENT

This invention relates to the treatment of residues obtained from the product of the reaction of a diolefin with a furfural. In accordance with another aspect, this invention relates to the treatment of residue remaining after recovery of a cotrimer of a diolefin and a furfural to produce useful products. In accordance with a further aspect, this invention relates to a pyrolysis treatment of residue produced by the reaction of diolefins with a furfural to produce products including diolefin, furfural, and additional cotrimer products. In accordance with a further aspect, this invention relates to an improved process for producing additional useful products from a normally waste residue material obtained following the reaction of a diolefin with furfural to produce cotrimers.

BACKGROUND OF THE INVENTION

The reaction of a diolefin, such as butadiene and its immediate homologs, with a furfural, such as furfural itself, and its immediate homologs, to produce cotrimers is a well-known reaction. This reaction can be carried out either in the presence or absence of water. It is also known that the reaction of a diolefin with furfural is accompanied by the formation of significant amounts of heavy materials that have no real useful purpose. The present invention is directed to an improved process for the treatment of the heavy materials to yield useful products.

Accordingly, an object of this invention is to produce useful products by the treatment of residue normally having no utility.

Another object of this invention is to provide an improved process for yielding additional reactants and products from a residue.

A further object of this invention is to produce useful products from the residues of the inter-reaction of a diolefin and a furfural.

Other objects, aspects as well as the several advantages of the invention will become apparent to one skilled in the art upon reading the accompanying disclosure and the appended claims.

SUMMARY OF THE INVENTION

In accordance with the invention, a process is provided for producing additional useful products by the thermal treatment of residues obtained from the cotrimer product formed by the reaction of a diolefin with a furfural by subjecting the residue to pyrolysis at an elevated temperature to produce substantial quantities of starting materials and cotrimer products.

More specifically, in accordance with the invention, a process is provided for producing additional useful products from cotrimer reaction mixtures formed by the reaction of a diolefin with a furfural by separating the cotrimer from the reaction mixture, and subjecting the heavier materials to pyrolysis at an elevated temperature sufficient to convert heavier materials to additional quantities of diolefin, furfural and cotrimer.

In accordance with a specific embodiment, butadiene is reacted with furfural to form a cotrimer reaction mixture and the product thus formed is subjected to distillation to recover cotrimer reaction product, leaving a residue (non-distillable) which is subjected to pyrolysis at a temperature of about 600° C. to recover substantial quantities of butadiene, furfural and cotrimer product.

DETAILED DESCRIPTION OF THE INVENTION

The reaction or inter-reaction of a diolefin and a furfural is well known in the art as set forth, for example, in U.S. Pat. No. 2,683,151, which is incorporated herein by reference. The conditions obtained during the inter-reaction to form the cotrimer products are conventional and can be carried out often in the presence of water as is done in the specific examples herein.

The product mixture formed by the reaction of a diolefin with furfural comprises cotrimer products and heavy, unidentifiable materials having a high boiling point. These products can be subjected to suitable operation techniques for separating the cotrimer from the heavier materials. One preferred method is to subject the cotrimer product to distillation under conditions which remove cotrimer product overhead leaving a residue of non-distillable materials as bottoms. Representative conditions useful in the distillation operation include an initial pressure of about 180 mg Hg and an initial kettle temperature of about 75° C. Distillate is collected at an initial head temperature of 40°–50° C. with sample collection continued until the kettle temperature reaches about 120° C. and a head temperature of 110° C. is reached. Sample collected up to this point comprises butadiene dimers and unreacted furfural. The kettle temperature is lowered below 100° C., and vessel pressure dropped to 2 mm Hg. Sample, comprising a small amount of furfural and mainly product cotrimer is collected overhead at head temperatures between 50°–110° C. with kettle temperatures of about 110°–160° C. required.

According to the invention, the residue is removed from the distillation kettle and is subjected to pyrolysis at an elevated temperature for a period of time sufficient to convert the heavier materials to additional quantities of diolefin, furfural and cotrimer. Ordinarily, the pyrolysis temperature should be in the range of about 500° to about 800° C., preferably on the order of about 550° to about 650° C. The period of time the thermal treatment can vary depending on the actual temperature employed, but will ordinarily range from about 1 to about 60 minutes.

Generally, the pyrolysis reaction is carried out in the absence of a catalyst, but in the event it is desired to facilitate the reaction it is within the scope of the invention to use a catalyst.

The pyrolysis of the invention can be conducted as a batch reaction for a suitable period of time under pyrolysis conditions or as a continuous process.

If desired, an inert gas such as nitrogen, carbon dioxide, helium, argon, and the like, or a mixture thereof, can be passed through the pyrolysis reaction zone in order to effectively sweep the pyrolysis products from the reaction zone to prevent subsequent side reactions of the desired products under the high temperatures employed in the reaction zone. The inert gas stream can be employed at any suitable range, but will generally be utilized at a gas hourly space velocity (GHSV) in the range of about 1 to about 500, preferably in the range of about 5 to about 200, standard volumes of inert gas per hour per volume of the pyrolysis reaction zone.

As is conventional in most pyrolysis reactions, the process of the present invention preferably employs particulate materials in the pyrolysis reaction zone providing increased surface area and an ability to transfer heat from the reaction zone to the feed material. For example, quartz chips, stainless steel chips, refractory oxides of various types including alumina, thoria, titania, and the like, and admixtures of any two or more thereof, can be utilized as the heat transfer material in the pyrolysis reaction zone. Such particulate materials can be in any of a variety of shapes and sizes, such as beads, chips, pellets, shavings, and the like as well as mixtures of any two or more thereof.

Following pyrolysis, the pyrolysis product comprising diolefin, furfural, and cotrimer, can be separated by any suitable conventional means, for example, distillation, solvent extraction, and the like. In a preferred mode of operation, the product from pyrolysis is separated by distillation as above.

It is within the scope of the invention to recycle the separated diolefin and furfural to the appropriate process step for conversion to additional cotrimer product. It is also possible to recycle any remaining polymeric residue to the pyrolysis zone for further conversion according to the instant invention.

The following examples are illustrative of the present invention. The reaction of furfural with butadiene and distillation of the resultant butadiene/furfural cotrimer product is described in Example I. The pyrolysis treatment of the distillation residue remaining in Example I is described according to the invention in Example II.

EXAMPLE I

A 1-L Stainless Steel Autoclave Engineers Magnedrive-stirred tank reactor was charged with 260 g (2.7 mol) of furfural. The reactor was sealed, pressured to 75 psig with $N_2$ while stirring the contents, then vented. This pressure, vent sequence was repeated a total of 4 times. After venting for the final time, the reactor was evacuated to about 40 mm Hg, sealed, and heated to 180° C. Once the desired reaction temperature was reached, butadiene was introduced until reactor pressure reached 100 psig. Thereafter, butadiene was introduced on demand as required to maintain a reactor pressure of 100 psig, so that over a period of 7½ hours, 101 g (1.9 mol) of butadiene had been added. The reactor was then cooled, vented, and emptied. 356.7 g of crude product was charged to a distillation pot for fractional distillation at reduced pressure (180 mm initially, reduced to 2 mm for final 50 g product collected). 345.3 g were collected overhead as unreacted furfural, by-products vinylcyclohexene and cyclooctadiene, and the desired cotrimer product, and 11.2 g of material did not distill. The distillation residue was further reacted as described in Example II.

EXAMPLE II 10 g of the distillation residue obtained as described above was warmed until it flowed. It was then poured into a 1" diameter×6" long quartz tube packed with 6-10 mesh quartz chips. A slow stream of nitrogen (0.4 SCFH) was passed through the tube. Exit gases were passed through a dry ice trap. The quartz tube was then placed in a furnace heated to 600° C. until no more condensate was observed (about 15 minutes).

5.6 of liquid was collected in the dry ice trap, and 4.1 g of char remained in the quartz tube. Gas chromatographic analysis of the material collected in the dry ice trap revealed:

0.6 g butadiene
1.0 g furfural
2.0 g cotrimer product
2.0 g heavier liquid

Thus, the inventive treatment of butadiene/furfural cotrimer distillation residue results in the recovery of significant additional quantities of cotrimer product as well as additional strarting materials useful upon recycle.

I claim:

1. A process for producing additional useful products by the treatment of polymeric residues formed upon reaction of a diolefin and a furfural which comprises subjecting said residue to pyrolysis at an elevated temperature in the range of about 500°–800° C. and for a period of time sufficient to convert said residue to additional quantities of diolefin, furfural, and desirable cotrimeric product.

2. A process according to claim 1 wherein said period of time ranges from about 1 to about 60 minutes.

3. A process according to claim 1 wherein said polymeric residue is formed by the reaction of 1,3-butadiene and furfural.

4. A process according to claim 1 wherein the polymeric residue formed by the reaction of diolefin and a furfural is subjected to separation to remove desirable cotrimer product from the reaction product leaving heavier residue which is subjected to pyrolysis at an elevated temperature in the range of about 500°–800° C. for a period of time ranging from about 1 to about 60 minutes.

5. A process according to claim 4 wherein the polymeric product is separated by distillation to remove overhead cotrimer and leave as heavier non-distillable products comprising said residue which is, in turn, subjected to pyrolysis to form additional quantities of reactant and desirable cotrimeric product.

6. A process according to claim 4 wherein the additional quantities of diolefin and furfural formed are recycled for use in the reaction of diolefin with furfural for production of cotrimers.

7. A process according to claim 4 wherein the reaction including the diolefin and furfural is carried out in the presence of water.

8. A process according to claim 7 wherein said polymer residue is formed by the reaction of 1,3-butadiene with furfural and said pyrolysis is carried out at a temperature in the range of about 550°–650° C.

* * * * *